United States Patent
Govari et al.

(10) Patent No.: US 12,004,804 B2
(45) Date of Patent: Jun. 11, 2024

(54) BASKET CATHETER WITH MUSHROOM SHAPE DISTAL TIP

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Kevin Justin Herrera, West Covina, CA (US); Alexander David Squires, Duarte, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 217 days.

(21) Appl. No.: 17/470,751

(22) Filed: Sep. 9, 2021

(65) Prior Publication Data

US 2023/0075838 A1 Mar. 9, 2023

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00077* (2013.01); *A61B 2018/00267* (2013.01); *A61B 2018/00357* (2013.01); *A61B 2018/00577* (2013.01); *A61B 2018/00613* (2013.01); *A61B 2018/1467* (2013.01)

(58) Field of Classification Search
CPC .......... A61B 2018/00613; A61B 2018/00577; A61B 2018/1467; A61B 5/6858
See application file for complete search history.

(56) References Cited

U.S. PATENT DOCUMENTS

| 4,699,147 A | 10/1987 | Chilson et al. |
| 4,940,064 A | 7/1990 | Desai |

(Continued)

FOREIGN PATENT DOCUMENTS

| CN | 111248993 A | 6/2020 |
| CN | 111248996 A | 6/2020 |

(Continued)

OTHER PUBLICATIONS

Extended European Search Report dated Feb. 28, 2023, from corresponding European Application No. 22194535.5.

*Primary Examiner* — Jaymi E Della
(74) *Attorney, Agent, or Firm* — Troutman Pepper Hamilton Sanders LLP

(57) ABSTRACT

Embodiments of the present invention include a medical probe having an insertion tube, a basket assembly, an axial electrode, and a plurality of radial electrodes. The insertion tube is configured for insertion into a body cavity of a patient. The basket assembly has a proximal end that is connected distally to the insertion tube and includes a plurality of resilient spines, which are configured to bow radially outward from an axis of the basket assembly and are conjoined at a distal end of the basket assembly. The axial electrode is disposed at the distal end of the basket assembly, having a diameter of at least 1.5 millimeters, and is configured to contact tissue in the body cavity. The plurality of radial electrodes are configured to contact the tissue in the body cavity and include radial electrodes disposed on the spines.

15 Claims, 4 Drawing Sheets

(56) References Cited

U.S. PATENT DOCUMENTS

| | | |
|---|---|---|
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,944,022 A | 8/1999 | Nardella et al. |
| 5,968,040 A | 10/1999 | Swanson et al. |
| 5,983,126 A | 11/1999 | Wittkampf |
| 6,014,579 A | 1/2000 | Pomeranz et al. |
| 6,014,590 A | 1/2000 | Whayne et al. |
| 6,119,030 A | 9/2000 | Morency |
| 6,216,043 B1 | 4/2001 | Swanson et al. |
| 6,216,044 B1 | 4/2001 | Kordis |
| 6,428,537 B1 | 8/2002 | Swanson et al. |
| 6,456,864 B1 | 9/2002 | Swanson et al. |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |

(56) References Cited

U.S. PATENT DOCUMENTS

| | | |
|---|---|---|
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2010/0076426 A1* | 3/2010 | de la Rama ......... A61B 5/0036 606/41 |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2012/0143298 A1 | 6/2012 | Just et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0039484 A1 | 2/2014 | Leung |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0303469 A1 | 10/2014 | Kordis et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0231729 A1* | 8/2015 | Yang ................. B23K 11/3009 219/92 |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0312012 A1* | 11/2017 | Harlev ............... A61B 1/00087 |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279896 A1 | 10/2018 | Ruppersberg |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1* | 3/2019 | Viswanathan ..... A61B 18/1492 |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |

(56) References Cited

U.S. PATENT DOCUMENTS

| | | |
|---|---|---|
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0230403 A1* | 7/2020 | Bowers ............... A61B 18/12 |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| EP | 0668740 A1 | 8/1995 |
| EP | 0644738 B1 | 3/2000 |
| EP | 1323451 A2 | 9/2002 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| JP | 2020517355 A | 7/2020 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020206328 A1 | 10/2020 |

* cited by examiner

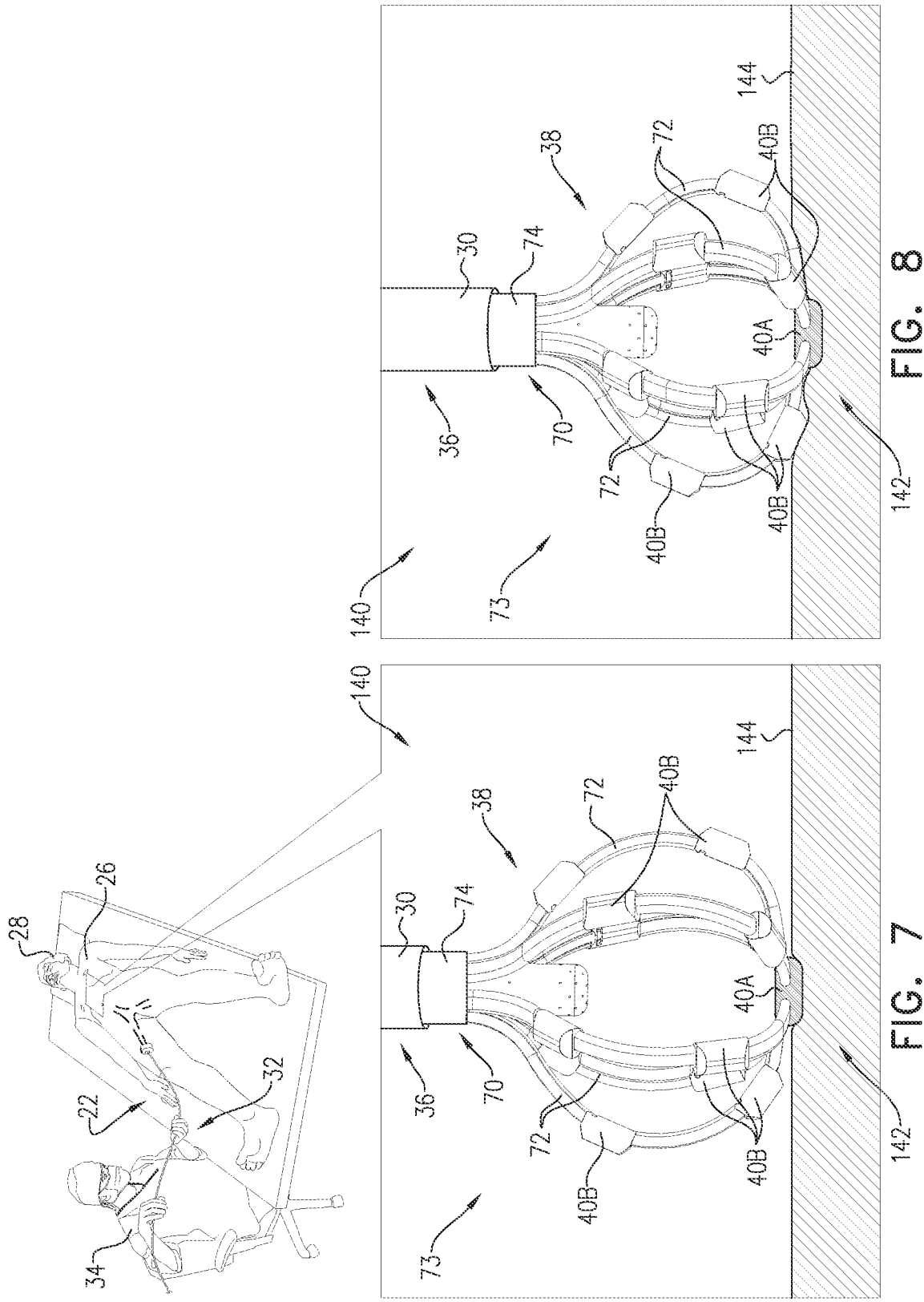

BASKET CATHETER WITH MUSHROOM SHAPE DISTAL TIP

FIELD OF THE INVENTION

The present invention relates generally to medical probes, and specifically to a medical probe comprising a mushroom-shaped ablation electrode affixed to a distal end of a basket assembly.

BACKGROUND OF THE INVENTION

Arrhythmias are abnormal heart rhythms that are typically caused by a small area of cardiac tissue that produces irregular heartbeats. Cardiac ablation is a medical procedure that can be performed to treat an arrhythmia by destroying the area of the cardiac tissue causing the irregular heartbeats. Some medical systems use irreversible electroporation (IRE) to ablate cardiac tissue. IRE is a nonthermal ablation method based on the unrecoverable permeabilization of cell membranes caused by short pulses of high voltage delivered to the tissue.

U.S. Patent Application 2016/0113582 to Altmann et al., describes a catheter with a distal tip comprising a micro-electrode array that can be used for acute focal mapping. The catheter comprises a basket assembly having a plurality of electrode-carrying spines. The distal tip has a nonmetallic, electrically insulating substrate body with indentations in which microelectrodes are positioned in a manner to present a generally smooth distal tip profile.

U.S. Patent Application 2012/0143298 to Just et al., describes an electrode assembly for a catheter. In one embodiment, the electrode assembly comprises one or more positioning electrodes and one or more ablation electrodes disposed at a distal end of a shaft. In another embodiment, the electrode assembly comprises a basket portion of the catheter having non-contact electrodes.

U.S. Patent Application 2018/0279896 to Ruppersberg describes a system and method for analyzing electrophysiological data. The system comprises an ablation module configured to deliver RF ablation energy to ablation electrodes disposed near a distal end of a catheter. In one embodiment, the system comprises a catheter having an elongated body that includes a tip electrode and a ground electrode that are electrically isolated from each other and can be used for electro-ablation of body tissue.

U.S. Patent Application 2014/0303469 to Kordis et al., describes a method for detecting cardiac rhythm disorders. The system uses a catheter comprising a basket assembly with spines that are used to guide a plurality of exposed electrodes that are configured to sense local electric voltages from endocardial surface of a heart.

U.S. Patent Application 2018/0344188 to Govari describes a catheter comprising a basket assembly. The basket assembly comprises plurality of spline electrodes disposed on splines of the assembly, and a far-field electrode is disposed in the interior of the assembly. The spline electrodes can be used to generate an intracardiac electrogram and the far-field electrode can be used to generate a far-field electrogram.

The description above is presented as a general overview of related art in this field and should not be construed as an admission that any of the information it contains constitutes prior art against the present patent application.

SUMMARY OF THE INVENTION

There is provided, in accordance with an embodiment of the present invention, a medical probe, including an insertion tube configured for insertion into a body cavity of a patient, a basket assembly having a proximal end that is connected distally to the insertion tube and including a plurality of resilient spines, which are configured to bow radially outward from an axis of the basket assembly and are conjoined at a distal end of the basket assembly, an axial electrode disposed at the distal end of the basket assembly, having a diameter of at least 1.5 millimeters, and configured to contact tissue in the body cavity, and a plurality of radial electrodes, which are configured to contact the tissue in the body cavity and include radial electrodes disposed on the spines.

In one embodiment, the medical probe further includes an electric signal generator coupled to the axial and the radial electrodes.

In another embodiment, the electrical signal generator is configured to deliver irreversible electroporation (IRE) pulses to the axial electrode. In some embodiments, the electric signal generator is configured to deliver IRE energy simultaneously to the axial electrode and at least one radial electrode. In other embodiments, the electrical signal generator is configured to deliver radio frequency energy to the axial electrode.

In an additional embodiment, the spines have respective outer sides and inner sides, and wherein each given radial electrode includes a conductive material biased towards the outer side of its respective spine.

In a further embodiment, the axial electrode is circularly shaped with a rounded surface. In some embodiments, the axial electrode has a thickness of at least 20% of the diameter. In other embodiments, the axial electrode has sides having a radius of curvature that is at least 25% of the thickness. In supplemental embodiments, the axial electrode has sides having a radius of curvature that is at most 50% of the thickness.

There is also provided, in accordance with an embodiment of the present invention, a method for fabricating a medical probe, including providing an insertion tube configured for insertion into a body cavity of a patient, providing a basket assembly having a proximal end that is connected distally to the insertion tube and including a plurality of resilient spines, which are configured to bow radially outward from an axis of the basket assembly and are conjoined at a distal end of the basket assembly, providing an axial electrode disposed at the distal end of the basket assembly, having a diameter of at least 1.5 millimeters, and configured to contact tissue in the body cavity, and providing a plurality of radial electrodes, which are configured to contact the tissue in the body cavity and include radial electrodes disposed on the spines.

There is additionally provided, in accordance with an embodiment of the present invention, a method for treatment, including inserting, into a body cavity, an insertion tube having a distal end containing a lumen passing through the insertion tube, deploying, into the body cavity from the distal end, a basket assembly having a proximal end that is connected distally to the insertion tube and including a plurality of resilient spines, which are configured to bow radially outward from an axis of the basket assembly and are conjoined at a distal end of the basket assembly, the basket assembly including an axial electrode disposed at the distal end of the basket assembly, having a diameter of at least 1.5 millimeters, and configured to contact tissue in the body cavity, and a plurality of radial electrodes, which are configured to contact the tissue in the body cavity and include radial electrodes disposed on the spines, positioning the basket assembly so that the axial electrode presses against tissue in the body cavity, and conveying, via the axial electrode, ablation energy to the tissue.

BRIEF DESCRIPTION OF THE DRAWINGS

The disclosure is herein described, by way of example only, with reference to the accompanying drawings, wherein:

FIGS. 7 and 8 are schematic pictorial illustrations of the basket assembly inside the chamber of the heart during the medical procedure, in accordance with an embodiment of the present invention.

DETAILED DESCRIPTION OF EMBODIMENTS

Overview

While a distal tip of a basket catheter may comprise a diagnostic electrode, constraints on the size of the electrode make it difficult to operate the electrode as an ablation electrode. In contrast to a diagnostic electrode, an ablation electrode must support transfer of relatively large currents without being damaged or deformed, as well as having sufficient surface area and geometry to avoid high current density which can create localized electrical arcing.

Embodiments of the present invention provide a medical probe comprising a basket assembly having an ablation electrode fixed to its distal end. As described hereinbelow, the medical probe comprises an insertion tube configured for insertion into a body cavity of a patient, and a basket assembly having a proximal end that is connected distally to the insertion tube, i.e., is connected to a distal end of the insertion tube. The basket assembly comprises a plurality of resilient spines, which are configured to bow radially outward from an axis of the basket assembly and are conjoined at a distal end of the basket assembly. The medical probe also comprises an axial electrode disposed at the distal end of the basket assembly, having a diameter of at least 1.5 millimeters (mm), and configured to contact tissue in the body cavity. In addition to the axial electrode, the medical probe further comprises a plurality of radial electrodes, which are configured to contact the tissue in the body cavity and which are disposed on the spines.

In some embodiments, the axial electrode is mushroom-shaped (i.e., a thick disc with a rounded surface), and has a contact area (i.e., because of the at least 1.5 mm described supra) large enough that provides sufficient lateral surface area to dissipate heat during an ablation procedure. In addition to increasing the surface area, the rounded surface of the axial electrode helps prevent arcing and is atraumatic to tissue.

System Description

Figure 1:
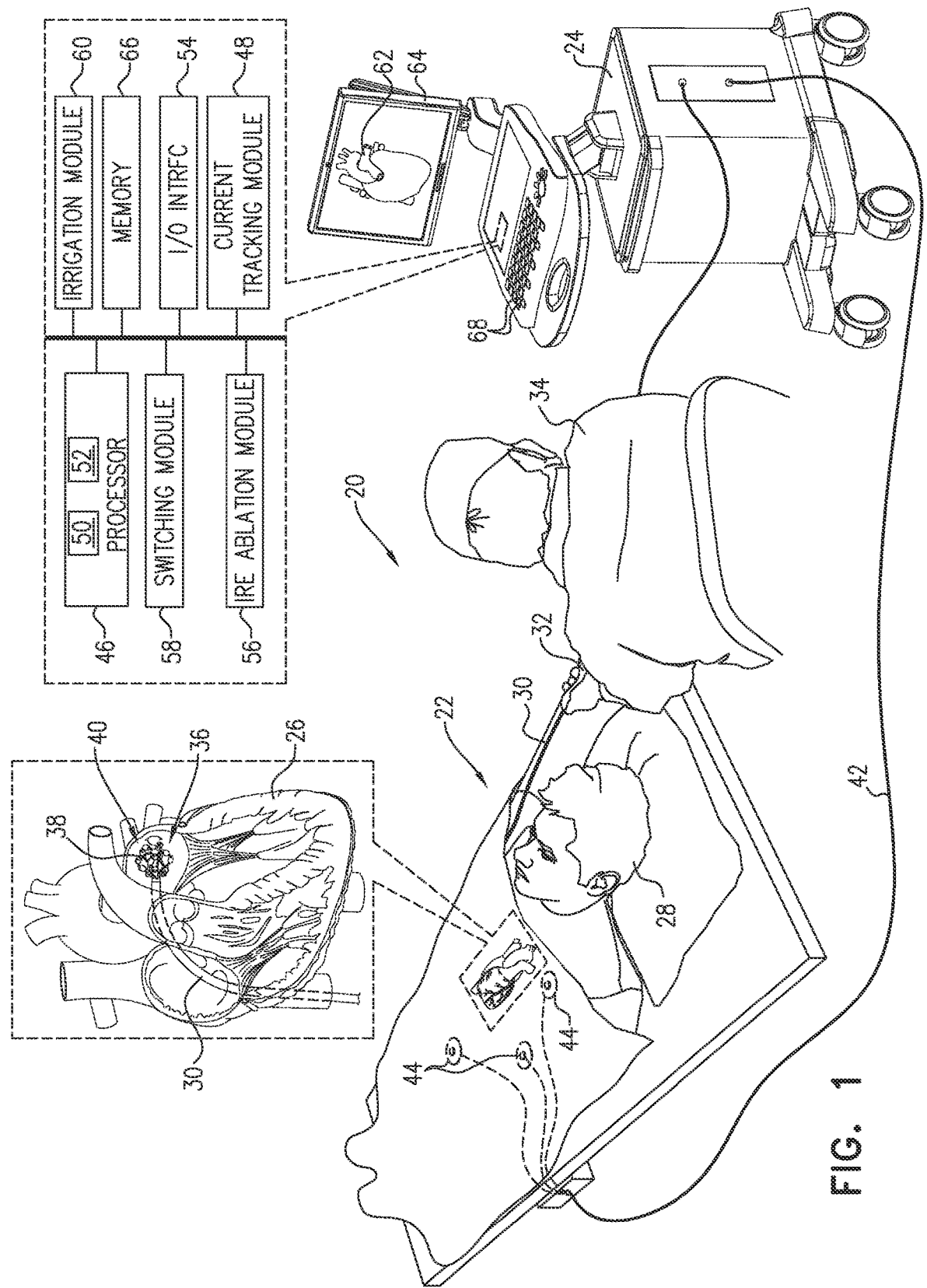
FIG. 1 is a schematic pictorial illustration of a medical system 20 comprising an axial electrode fixed to a distal end of a basket assembly, in accordance with an embodiment of the present invention.

FIG. 1 is a schematic, pictorial illustration of a medical system 20 comprising a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Probe 22 comprises a flexible insertion sheath 30 and a handle 32 coupled to a proximal end of the insertion sheath. Probe 22 also comprises a flexible insertion tube 74 that is contained within insertion sheath 30. During a medical procedure, a medical professional 34 can insert probe 22 through the vascular system of patient 28 so that a distal end 36 of insertion sheath 30 enters a body cavity such as a chamber of heart 26. Upon distal end 36 entering the chamber of heart 26, medical professional 34 can deploy a basket assembly 38 affixed to a distal end 73 of insertion tube 74. Basket assembly 38 comprises a set of electrodes 40, as described in the description referencing FIG. 2 hereinbelow.

To start performing a medical procedure such as irreversible electroporation (IRE) ablation, medical professional 34 can manipulate handle 32 to position distal end 73 so that one or more electrodes 40 engage cardiac tissue at a desired location or locations.

In the configuration shown in FIG. 1, control console 24 is connected, by a cable 42, to body surface electrodes, which typically comprise adhesive skin patches 44 that are affixed to patient 28. Control console 24 comprises a processor 46 that, in conjunction with a current tracking module 48, determines location coordinates of distal end 73 inside heart 26 based on impedances and/or currents measured between adhesive skin patches 44 and electrodes 40 that are affixed to basket assembly 38. In addition to being used as location sensors during a medical procedure, electrodes 40 may perform other tasks such as ablating tissue in the heart.

As described hereinabove, in conjunction with current tracking module 48, processor 46 may determine location coordinates of distal end 73 inside heart 26 based on impedances and/or currents measured between adhesive skin patches 44 and electrodes 40. Such a determination is typically after a calibration process relating the impedances or currents to known locations of distal end 73 has been performed. While embodiments presented herein describe electrodes 40 that are (also) configured to deliver IRE ablation energy to tissue in heart 26, configuring electrodes 40 to deliver any other type of ablation energy to tissue in any body cavity is considered to be within the spirit and scope of the present invention.

Processor 46 may comprise real-time noise reduction circuitry 50 typically configured as a field programmable gate array (FPGA), followed by an analog-to-digital (A/D) signal conversion integrated circuit 52. The processor can be programmed to perform one or more algorithms disclosed herein, each of the one or more algorithms comprising steps described hereinbelow. The processor uses circuitry 50 and circuit 52 as well as features of modules which are described in more detail below, in order to perform the one or more algorithms.

Although the medical system shown in FIG. 1 uses impedance or current-based sensing to measure a location of distal end 73, other location tracking techniques may be used (e.g., techniques using magnetic-based sensors). Impedance and current-based location tracking techniques are described, for example, in U.S. Pat. Nos. 5,983,126, 6,456,864 and 5,944,022. The methods of location sensing described hereinabove are implemented in the above-mentioned CARTO® system and are described in detail in the patents cited above.

Control console 24 also comprises an input/output (I/O) communications interface 54 that enables control console 24 to transfer signals from, and/or transfer signals to electrodes 40 and adhesive skin patches 44. In the configuration shown in FIG. 1, control console 24 additionally comprises an electric signal generator 56 and a switching module 58. While embodiments described herein present the electric signal generator as IRE ablation module 56 (i.e., electric signal generator 56 is also referred to herein as IRE ablation module 56), other types of electric signal generators are considered to be within the spirit and scope of the present invention. For example, electric signal generator 56 may be configured to generate radio frequency (RF) energy.

IRE ablation module 56 can be configured to generate IRE pulses comprising peak power in the range of tens of kilowatts. As described hereinbelow, medical system 20 performs IRE ablation by IRE ablation module 56 delivering IRE pulses to pairs of electrodes 40 simultaneously. In some embodiments, a given pair of the electrodes comprises two sets of electrodes 40 with each of the sets having at least one electrode 40. Using switching module 58, IRE ablation module 56 can deliver one or more IRE pulses independently to each of the pairs of the electrodes.

In order to dissipate the heat and to improve the efficiency of the ablation process, system 20 supplies irrigation fluid (e.g., a normal saline solution) to distal end 73 via a channel (not shown) in insertion tube 74. Control console 24 comprises an irrigation module 60 to monitor and control irrigation parameters, such as the pressure and the temperature of the irrigation fluid.

Typically, based on signals received from electrodes 40 and/or adhesive skin patches 44, processor 46 can generate an electroanatomical map 62 that shows the location of distal end 73 in the patient's body. During the procedure, processor 46 can present map 62 to medical professional 34 on a display 64, and store data representing the electroanatomical map in a memory 66. Memory 66 may comprise any suitable volatile and/or non-volatile memory, such as random-access memory or a hard disk drive.

In some embodiments, medical professional 34 can manipulate map 62 using one or more input devices 68. In alternative embodiments, display 64 may comprise a touchscreen that can be way configured to accept inputs from medical professional 34, in addition to presenting map 62.

Figure 2:
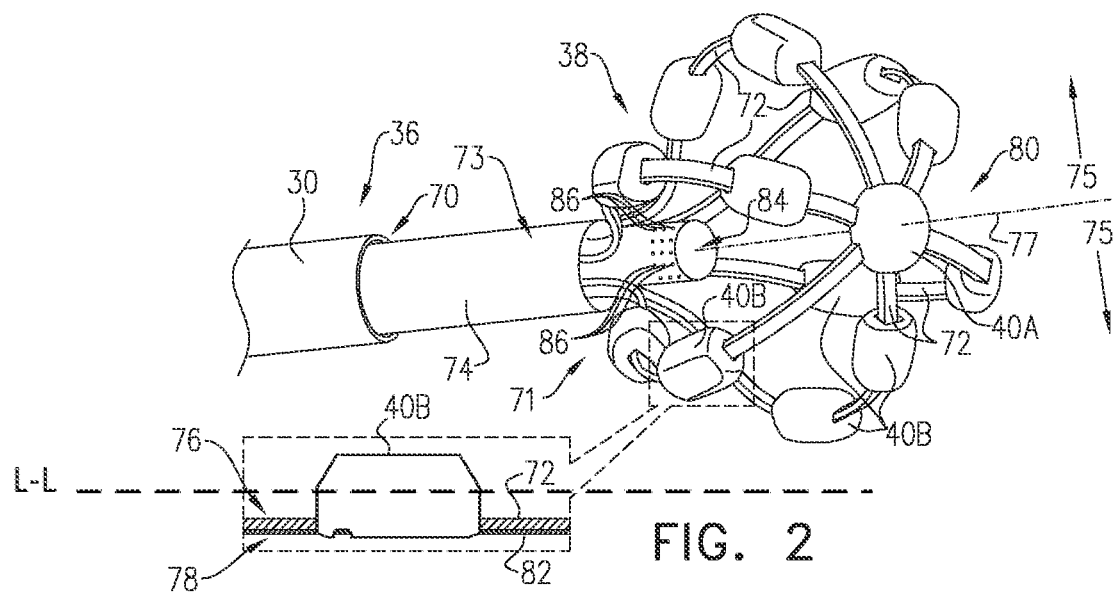
FIG. 2 is a schematic illustration of the basket assembly in an expanded configuration, in accordance with an embodiment of the present invention.

FIG. 2 is a schematic illustration of distal end 73 comprising basket assembly 38 in an expanded configuration, in accordance with an embodiment of the present invention. Basket assembly 38 can assume an expanded configuration when unconstrained, such as by being advanced out of an insertion sheath lumen 70 of insertion sheath 30.

In FIG. 2, electrodes 40 can be differentiated by appending a letter to the identifying numeral, so that the electrodes comprise electrodes 40A and 40B. In embodiments herein, electrode 40A may also be referred to as axial electrode 40A and electrodes 40B may also be referred to as radial electrodes 40B.

By way of example, basket assembly 38 comprises a plurality of resilient spines 72 that are formed at a distal end 73 insertion tube 74. A proximal end 71 of basket assembly 38 is connected to distal end 73 of insertion tube 74, and spines 72 are cojoined at a distal end 80 of the basket assembly (FIG. 2).

During a medical procedure, medical professional 34 can deploy basket assembly 38 by extending insertion tube 74 from distal end 36 of insertion sheath 30. Spines 72 may have oval (e.g., elliptical or circular) or rectangular (that may appear to be flat) cross-sections, and typically comprise a flexible, resilient material (e.g., a shape-memory alloy such as nickel-titanium, also known as Nitinol). In its expanded configuration, basket assembly 38 has an expanded arrangement wherein spines 72 bow in a radially outward direction 75 from a longitudinal axis 77 of the basket assembly.

In the configuration shown in FIG. 2, one or more electrodes 40B are inserted on to each given spine 72 so as to fit the electrodes to the spines. Each spine 72 has an outer side 76 and an inner side 78. In embodiments of the present invention, for a given radial electrode 40B fitted to a given spine 72, the given spine is assumed to be planar at the given radial electrode, wherein the plane divides the given electrode asymmetrically so that there is more conductive material on the outer side (of the plane) than on the inner side. In the inset of FIG. 2 showing a side view of electrode 40B, the spine 72 extends through the electrode 40B such that the spine 72 is offset or "asymmetric" with respect to the center line L-L by being on one side of center line L-L. With the spine 72 offset (by being on one side of center line L-L), electrode 40B will have more of its upper surface (inset of FIG. 2) extending into biological tissues.

In these embodiments, each electrode 40 (i.e., when fitted to a given spine 72) comprises a conductive material that is geometrically biased towards the outer sides of its respective spine 72, because of the asymmetry referred to above. Therefore, each given radial electrode 40B has a greater surface area on its outer side compared to the surface area of the given electrode on its inner side. By biasing radial electrodes 40B to outer side 76, the radial electrodes deliver more ablation energy from the portion of the radial electrodes outer side of the spines (i.e., significantly more than the ablation energy delivered from the portion of the radial electrodes on the inner side of the spines).

In embodiments of the present invention, probe 22 also comprises axial electrode 40A disposed at distal end 80 of basket assembly 38. Axial electrode 40A has a circular shape, and is described in FIGS. 3-5 hereinbelow. The three spines 72 can be affixed (e.g. welding, brazing or glued) to each other at the intersection of the spines 72 of the distal end 80 of the basket 38. The electrode 40A may have its outer surface affixed (e.g., welding, brazing or glued) to the outer surface of the one or more of the three spines intersecting at the distal end 80 of basket 38.

In embodiments described herein, electrodes 40 can be configured to deliver ablation energy to tissue in heart 26. In addition to using electrodes 40 to deliver ablation energy, the electrodes can also be used to determine the location of basket assembly 38 and/or to measure a physiological property such as local surface electrical potentials at respective locations on tissue in heart 26.

Examples of materials ideally suited for forming electrodes 40 include gold, platinum and palladium (and their respective alloys). These materials also have very high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 26.

Probe 22 also comprises a set of wires 82 that couple IRE ablation module 56 to electrodes 40. In some embodiments each spine 72 comprises at least one wire 82 affixed to its inner side 78.

In some embodiments, distal end 80 of basket assembly 38 comprises a stem 84 that extends longitudinally from distal end 73 of insertion tube 74. As described supra, control console 24 comprises irrigation module 60 that delivers irrigation fluid to distal end 73. Stem 84 comprises multiple spray ports 86, wherein each given spray port 86 is angled to aim delivery of the irrigation fluid to either a given electrode 40 or to tissue in heart 26 (i.e., by aiming the delivery between two adjacent spines 72).

Since electrodes 40 do not comprise spray ports that deliver irrigation fluid, the configuration described hereinabove enables heat to be transferred from the tissue (i.e., during an ablation procedure) to the portion of the electrodes on the inner side of the spines, and the electrodes can be cooled by aiming the irrigation fluid, via spray ports 86, at the portion of the electrodes on the inner side of the spines.

Figure 3:
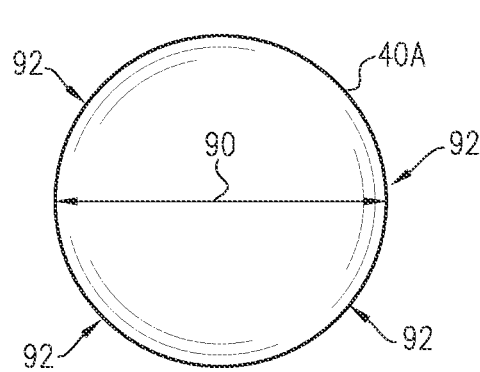
FIG. 3 is a schematic latitudinal view of the axial electrode, in accordance with an embodiment of the present invention.

FIG. 3 is a schematic latitudinal (i.e., top-down) view of axial electrode 40A, in accordance with an embodiment of the present invention. In embodiments of the present invention, axial electrode 40A is configured to deliver ablation energy (i.e., from IRE ablation module 56) to tissue in heart 26. Therefore, axial electrode 40A can have a diameter 90 (i.e., between sides 92 of the axial electrode) of at least 1.5 millimeters (mm). Typical values of diameter 90 are 1.5, 1.75, 2.0, 2.25, 2.5 mm and 3.0 mm. These large diameters also provide axial electrode 40A with sufficient lateral surface area to dissipate heat during ablation.

Figure 4:
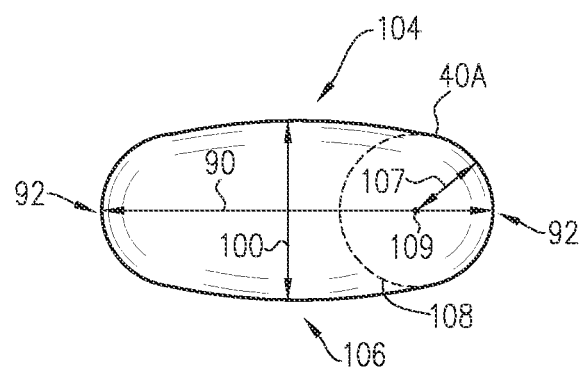
FIG. 4 is a schematic side view of the axial electrode, in accordance with an embodiment of the present invention.

FIG. 4 is a schematic side view of axial electrode 40A, in accordance with an embodiment of the present invention. In some embodiments, axial electrode 40A has a minimum thickness 100 (i.e., due to the rounded surface of the axial electrode) that is at least 20% of diameter 90.

In embodiments of the invention, axial electrode 40A has a rounded surface 102 comprising a distal end 104, a proximal end 106 and sides 92 that are all rounded. Therefore, surface 102 has no edges. In some embodiments, sides 92 are typically rounded so as to have a largest possible radius of curvature 107, while not creating an edge. Therefore, radius of curvature 107 can be between (at least) one-quarter (25%) of thickness 100 and (at most) one-half (50%) of thickness 100. The smallest radius of curvature of sides 92 typically occurs at terminal points of diameter 90, and is indicated schematically in the figure by a circle 108, with a center 109, that is tangential to one of the terminal points of diameter 90.

As described supra, axial electrode 40A has a mushroom-like shape (or a biscuit-like shape) whose rounded surface 102 and thickness constraints (a) make the axial electrode atraumatic to an engaged tissue in heart 26 (or tissue in any other body cavity in patient 28), (b) prevents high current density that can cause arcing during IRE ablation, (c) provides the axial electrode with sufficient surface area to dissipate heat during ablation, and (d) provides greater maneuverability for the axial electrode.

Figure 5:
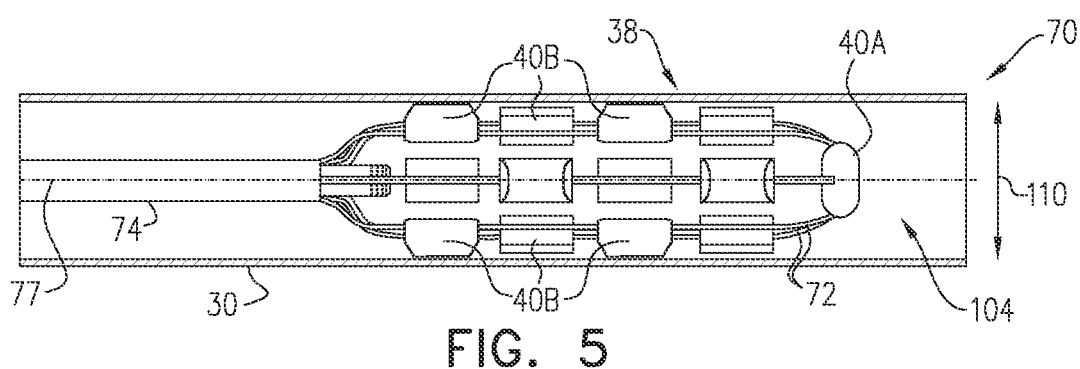
FIG. 5 is a schematic side view of the basket assembly in a collapsed configuration, in accordance with an embodiment of the present invention.

FIG. 5 is a schematic side view of basket assembly 38 in a collapsed configuration and arranged generally along longitudinal axis 77, in accordance with an embodiment of the present invention. As shown in FIG. 5, the outward bias of electrodes 40 enable spines 72 to lay flush with insertion tube 74 when basket assembly 38 is collapsed within insertion sheath 30.

In some embodiments, lumen 70 has a lumen diameter 110 between 3.0 and 3.33 mm (i.e., medical probe 22 is a 10 French catheter). In these embodiments, diameter 90 of axial electrode 40A is less than lumen diameter 110 so as to enable basket assembly 38 to traverse lumen 70.

Figure 6:
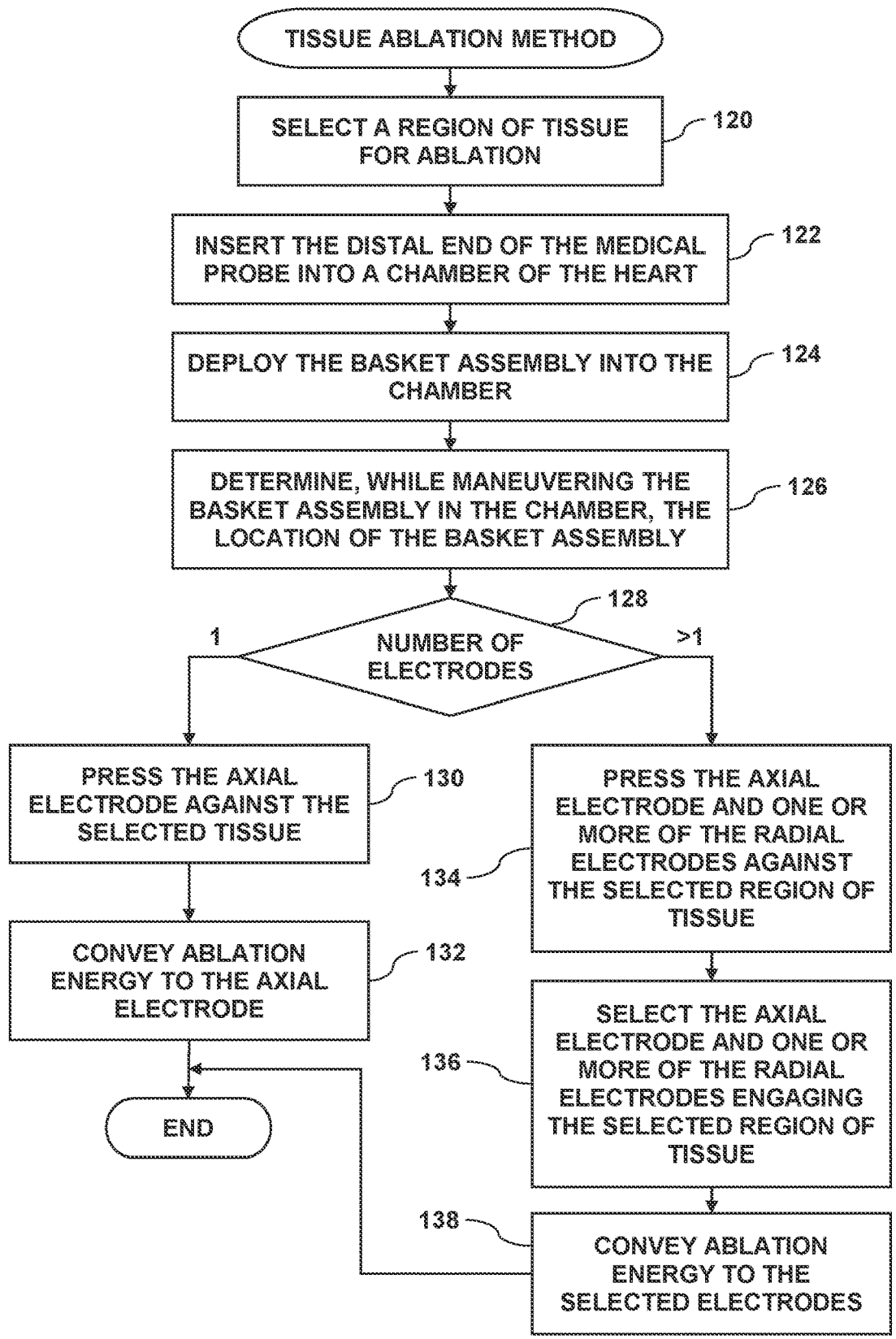
FIG. 6 is a flow diagram that schematically illustrates a method of using the axial electrode to perform a tissue ablation medical procedure in a chamber of a heart, in accordance with an embodiment of the present invention.

FIG. 6 is a flow diagram that schematically illustrates a method of using medical probe 22 to perform a tissue ablation medical procedure in a chamber 140 of heart 26, and FIGS. 7 and 8 are schematic pictorial illustrations of distal end 73 inside the chamber of the heart during the medical procedure, in accordance with an embodiment of the present invention.

In a tissue selection step 120, medical professional 34 selects a region 142 of intracardial tissue 144, and in an insertion step 122, the medical professional inserts distal end 36 of insertion sheath 30 into chamber 140 of heart 26.

In a deployment step 124, medical professional deploys basket assembly 38 from lumen 70 to chamber 140.

As medical professional 34 maneuvers the basket assembly within the chamber (e.g., by manipulating handle 32), processor 46 determines, in a location determination step 126, the location(s) of the basket assembly within the chamber. In some embodiments, processor 46 can present, to medical professional 34 (i.e., in map 62 on display 64), the location(s) of basket assembly 38.

In an ablation type selection step 128, if medical professional 34 wants to solely use axial electrode 40A to ablate the selected region of tissue 144, then in a first positioning step 130, medical professional 34 positions basket assembly 38 so that axial electrode 40A presses against the selected region on intracardiac tissue 144, as shown in FIG. 7.

In first ablation step 132, in response to an input from medical professional 34, IRE ablation module 56 conveys IRE pulses to axial electrode 40A, which the axial electrode delivers to the selected region of intracardiac tissue 144, and the method ends. In some embodiments, IRE ablation module 56 can receive the input from a given input device 68 or from an additional input device (not shown) on handle 32.

While embodiments herein describe IRE ablation module 56 delivering IRE pulses to one or more electrodes 40 so as to ablate intracardiac tissue 144, configuring medical system 20 to deliver, to any electrode 40, other types of ablation energy (e.g., radiofrequency energy) is considered to be within the spirit and scope of the present invention.

Returning to step 128, if medical professional 34 wants to use one or more pairs of electrodes 40 that comprise axial electrode 40A, then in a second positioning step 134, medical professional 34 positions basket assembly 38 so that axial electrode 40A and one or more radial electrodes 40B press against the selected region on intracardiac tissue 144, as shown in FIG. 8.

In an electrode selection step 136, medical professional 34 selects (e.g., using a given input device 68) axial electrode and at least one radial electrode 40B that is engaging intracardiac tissue 144, and in a second ablation step 138, in response to an input from medical professional 34, IRE ablation module 56 conveys IRE pulses to the selected electrodes, which the selected electrodes deliver to the selected region of intracardiac tissue 144, and the method ends.

In one embodiment, the selected electrodes comprise pairs of electrodes 40. In these embodiments, medical system 20 performs IRE ablation by delivering IRE pulses to pairs of electrodes 40. In additional embodiments, a given pair of the electrodes comprises two sets of electrodes 40 with each of the sets having at least one electrode 40. The electrodes in any given pair may be fixed to a single spine 72 or to multiple spines 72. Using switching module 58, IRE ablation module 56 can deliver one or more IRE pulses independently to each of the pairs of the electrodes.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical probe, comprising:
 an insertion tube configured for insertion into a body cavity of a patient;
 a basket assembly having a proximal end that is connected distally to the insertion tube and comprising a plurality of resilient spines, which are configured to bow radially outward from an axis of the basket assembly and are conjoined at a distal end of the basket assembly;
 an axial electrode attached to the plurality of resilient spines and disposed at the distal end of the basket assembly, the axial electrode configured to contact tissue in the body cavity and comprising:
  a circular shape with a rounded surface;
  a diameter of at least 1.5 millimeters;
  a thickness of at least 20% of the diameter; and
  sides having a radius of curvature of at least 25% and at most 50% of the thickness; and
 a plurality of radial electrodes disposed on the plurality of resilient spines which are configured to contact the tissue in the body.

2. The medical probe according to claim 1, and further comprising an electrical signal generator coupled to the axial and the plurality of radial electrodes.

3. The medical probe according to claim 2, wherein the electrical signal generator is configured to deliver irreversible electroporation (IRE) pulses to the axial electrode.

4. The medical probe according to claim 2, wherein the electrical signal generator is configured to deliver IRE energy simultaneously to the axial electrode and at least one of the plurality radial electrodes.

5. The medical probe according to claim 2, wherein the electrical signal generator is configured to deliver radio frequency energy to the axial electrode.

6. The medical probe according to claim 1, wherein the plurality of resilient spines have respective outer sides and inner sides, and wherein each of the plurality of radial electrodes comprises a conductive material biased towards the outer side of a respective spine of the plurality of resilient spines.

7. The medical probe of claim 1, further comprising a stem that extends longitudinally from a distal end of the insertion tube along a longitudinal axis of the basket assembly, wherein a distance from the stem to the axial electrode decreases as the basket assembly moves from a collapsed configuration to an expanded configuration.

8. A method for fabricating a medical probe, comprising:
 providing an insertion tube configured for insertion into a body cavity of a patient;
 connecting a proximal end of a basket assembly to a distal end of the insertion tube, the basket assembly comprising a plurality of resilient spines, which are configured to bow radially outward from an axis of the basket assembly and are conjoined at a distal end of the basket assembly;
 providing an axial electrode attached to the plurality of resilient spines and disposed at the distal end of the basket assembly, the axial electrode configured to contact tissue in the body cavity and comprising:
  a circular shape with a rounded surface;
  a diameter of at least 1.5 millimeters;
  a thickness of at least 20% of the diameter; and
  sides having a radius of curvature of at least 25% and at most 50% of the thickness; and
 providing a plurality of radial electrodes disposed on the plurality of resilient spines which are configured to contact the tissue in the body cavity.

9. The method according to claim 8, and further comprising providing an electrical signal generator coupled to the axial and the plurality of radial electrodes.

10. The method according to claim 9, wherein the electrical signal generator is configured to deliver irreversible electroporation (IRE) pulses to the axial electrode.

11. The method according to claim 9, wherein the electrical signal generator is configured to deliver IRE energy simultaneously to the axial electrode and at least one of the plurality of radial electrodes.

12. The method according to claim 9, wherein the electrical signal generator is configured to deliver radio frequency energy to the axial electrode.

13. The method according to claim 8, wherein each of the plurality of resilient spines have respective outer sides and inner sides, and wherein each of the plurality of radial electrodes comprises a conductive material biased towards the outer side of a respective spine of the plurality of resilient spines.

14. A method for treatment, comprising:
 inserting, into a body cavity, an insertion tube having a distal end containing a lumen passing through the insertion tube;
 deploying, into the body cavity from the distal end, a basket assembly having a proximal end that is connected distally to the insertion tube and comprising a plurality of resilient spines, which are configured to bow radially outward from an axis of the basket assembly and are conjoined at a distal end of the basket assembly, the basket assembly comprising:
  an axial electrode attached to the plurality of resilient spines and disposed at the distal end of the basket assembly, the axial electrode configured to contact tissue in the body cavity and comprising:
  a circular shape with a rounded surface;
  a diameter of at least 1.5 millimeters;
  a thickness of at least 20% of the diameter; and
  sides having a radius of curvature of at least 25% and at most 50% of the thickness, and
  a plurality of radial electrodes disposed on the plurality of resilient spines which are configured to contact the tissue in the body;
 positioning the basket assembly so that the axial electrode presses against the tissue in the body cavity; and
 conveying, via the axial electrode, ablation energy to the tissue.

15. The medical probe of claim 7, wherein the stem comprises one or more spray ports to deliver irrigation fluid to the tissue in the body cavity, the axial electrode, an electrode of the plurality of radial electrodes, or a combination thereof.

* * * * *